United States Patent [19]

Hutson, Jr. et al.

[11] 4,229,609

[45] Oct. 21, 1980

[54] PROCESS FOR DEHYDROGENATING HYDROCARBONS

[75] Inventors: Thomas Hutson, Jr.; Francis M. Brinkmeyer, both of Bartlesville, Okla.

[73] Assignee: Phillips Petroleum Company, Bartlesville, Okla.

[21] Appl. No.: 18,689

[22] Filed: Mar. 8, 1979

[51] Int. Cl.$^2$ .............................................. C07C 5/36
[52] U.S. Cl. .................................. 585/660; 585/661; 585/663
[58] Field of Search .............................. 585/660, 661

[56] References Cited

U.S. PATENT DOCUMENTS

| | | | |
|---|---|---|---|
| 2,364,453 | 12/1944 | Layng et al. | 585/420 |
| 3,027,237 | 3/1962 | McMullan | 23/199 |
| 3,461,183 | 8/1969 | Hepp | 585/660 |
| 3,539,651 | 11/1970 | Hepp | 585/660 |
| 3,542,897 | 11/1970 | Wattimena | 585/663 |
| 3,600,457 | 8/1971 | Milloy | 585/661 |
| 3,641,182 | 2/1972 | Box et al. | 585/660 |
| 3,670,044 | 6/1972 | Drehman | 585/661 |
| 3,883,418 | 5/1975 | Drehman et al. | 208/138 |
| 3,894,110 | 7/1975 | Drehman | 585/660 |
| 3,957,688 | 5/1976 | Farha et al. | 252/466 PT |

*Primary Examiner*—Veronica O'Keefe

[57] ABSTRACT

A continuous process for dehydrogenating hydrocarbons comprising repetitively carrying out dehydrogenation using a steam active dehydrogenation catalyst and regenerating of said catalyst with steam and oxygen-containing gas wherein the flow rate of steam is maintained constant during both the dehydrogenation and the regeneration and wherein the catalyst is purged with steam prior to each dehydrogenation and each regeneration.

15 Claims, No Drawings

PROCESS FOR DEHYDROGENATING HYDROCARBONS

This invention relates to an improved process for the dehydrogenation of a dehydrogenatable hydrocarbon feed. In another aspect this invention relates to an improved process for regenerating a dehydrogenation catalyst.

Numerous catalysts are known in the art as being suitable, to varying degrees, for the dehydrogenation of dehydrogenatable hydrocarbons in the presence of steam. Examples of such catalysts are disclosed in U.S. Pat. No. 3,670,044; U.S. Pat. No. 3,957,688; U.S. Pat. No. 3,894,110; U.S. Pat. No. 3,641,182; U.S. Pat. No. 3,539,651; and U.S. Pat. No. 3,461,183, the disclosure of which are incorporated herein by reference.

It is also known in the art that such dehydrogenation catalysts will decline in activity during use. The decline in activity is generally believed to be due to the formation of coke and polymers on the catalyst. In order to maintain catalyst activity it has therefore been necessary to periodically regenerate the catalyst. Generally, this has been done by cutting off the feed to the catalyst and then treating the catalyst with steam diluted air.

An object of the present invention is to provide a new method for regenerating the steam active catalyst which allows for the elimination of large and expensive switching valves on the steam lines.

Another object of this invention is to provide a process in which the steam preheater can operate more efficiently.

Another object of this invention is to provide a process in which heat in the regeneration steam can be more efficiently used.

Other aspects, objects, and advantages of the present invention will be apparent from a reading of the following disclosure.

In accordance with the instant invention, a process is provided for dehydrogenating a dehydrogenatable hydrocarbon feed using a bed of steam active dehydrogenation catalyst which is repetitively regenerated with steam and oxygen-containing gas wherein the flow rate of steam through the catalyst bed is maintained constant. More specifically the process involves passing dehydrogenatable hydrocarbon feed through the catalyst bed under dehydrogenation conditions for a period of time, then stopping the flow of dehydrogenatable hydrocarbon to the catalyst bed, then after the steam has purged at least part of the dehydrogenatable hydrocarbon from the catalyst bed passing oxygen-containing gas through the catalyst bed under regeneration conditions for a period of time, then stopping the flow of oxygen-containing gas to the catalyst bed, then after the steam has purged at least part of the oxygen from the catalyst bed passing dehydrogenatable hydrocarbon through the catalyst bed under dehydrogenation conditions.

The present invention is applicable to any dehydrogenation employing a steam active dehydrogenation catalyst. The process is particularly suitable for use when the steam active dehydrogenation catalyst comprises (1) a support selected from the group consisting of alumina, silica, magnesia, zirconia, alumina-silicates, Group II aluminate spinels and mixtures thereof and (2) a catalytic amount of at least one Group VIII metal. (Groups of metals as referred to herein are the groups of metals as classified in the Periodic Table of the Elements as set forth in Chemical Rubber Company's "Handbook of Chemistry and Physics", 45th Edition (1964), page B-2).

Any catalytically active amount of Group VIII metal can be employed in the steam active dehydrogenation catalysts. Generally the Group VIII metal is present in the catalyst in an amount in the range of about 0.01 to about 10 weight percent of the weight of the support, more often about 0.1 to about 5 weight percent.

Other suitable copromoter metals can also be employed in the steam active dehydrogenation catalyst in conjunction with the Group VIII metal. A preferred type of such co-promoters are Group IVa metals selected from the group of lead, tin, and germanium. The Group IVa metal can exist in the range of about 0.01–10 weight percent of said support, and in one embodiment, can exist in the range of about 0.1–1 weight percent of said support, and in one further embodiment, can exist in the range of about 0.1–0.5 weight percent of said support. Although any Group IVa metal, when in compound form, is fully within the scope of this invention, some convenient compounds are the halides, nitrates, oxalates, acetates, carbonates, propionates, tartrates, bromates, chlorates, oxides, hydroxides, and the like of tin, germanium and lead. Tin, itself, is the preferred Group IVa metal and impregnation of the supports with tin compounds such as the stannous halides is particularly effective and convenient.

Generally speaking, the Group VIII and Group IVa compounds, which can be combined with the supports to form the catalysts used in the present invention, can be any compound in which all elements, other than those of Group VIII, or Group IVa, are volatilized during calcination. These compounds can be sequentially combined with the support, in any order, or for convenience, can be applied simultaneously in a single impregnation operation. After impregnation, the composite solids are dried and calcined.

The dehydrogenation steps are conducted under any suitable conditions. Generally, the dehydrogenation is carried out such that the temperature in the inlet portion of the catalyst beds is at a temperature in the range of about 950° F. to about 1,150° F., preferably about 1080° F. to about 1120° F. The dehydrogenation is also conducted at a pressure in the range of about 0 to about 200 psig, preferably about 0 to about 100 psig. Generally, the molar ratio of steam to hydrocarbon is in the range of about 1/1 to about 25/1, preferably about 2/1 to 15/1. The use of an externally heated reactor, i.e. a reactor within a fired furnace, enables one to carry out the present invention with the lower levels of steam. The liquid hourly space velocity of hydrocarbon, i.e. volume of hydrocarbon per volume of catalyst per hour, is generally in the range of about 1 to about 6, preferably about 1.5 to about 3. It is often preferable to include hydrogen with the hydrocarbon feed. The molar ratio of hydrogen to hydrocarbon is generally in the range of about 0.3/1 to about 1.3/1, preferably about 0.5/1 to about 0.8/1.

The regeneration steps can also be conducted under any suitable conditions. Generally the temperature and pressure of the catalyst bed is as in the dehydrogenation steps. Oxygen is employed in the steam in an amount in the range of about 0.5 to about 2.5 mole percent of the moles of steam.

The hydrocarbon feed can be any dehydrogenatable hydrocarbon. The process is particularly suitable for hydrocarbons boiling in the gasoline range, particularly hydrocarbons having 6 to 9 carbon atoms per molecule.

It has also been found desirable to include nitrogen in the steam during the purging steps that are employed between dehydrogenation and regeneration. Any amount of nitrogen can be employed that will assist in the purging of material from the catalyst bed.

The present invention is particularly well adapted for use in a process which uses more than one catalyst bed. When more than one catalyst bed is employed, it is possible to carry on dehydrogenation of one bed while regeneration is being conducted in another, thus minimizing or eliminating the interruption of hydrocarbon feed conversion. The flows of hydrocarbon feed and steam need not be interrupted but instead only diverted. The instant flow rate of hydrocarbons feed and steam allows for the respective preheaters to operate under a constant load, which is more efficient in terms of energy usage. Using more than one catalyst bed also enables one to make more efficient use of the steam because one can use the effluent from a bed that is being regenerated to indirectly heat the hydrocarbon feed that is being supplied to a bed where dehydrogenation is being carried out. It is also possible to use the effluent from the catalyst beds to indirectly heat water to produce additional low pressure steam for use in the process.

A further understanding of the present invention will be provided by the following specific example.

EXAMPLE

A dehydrogenatable hydrocarbon feed having about 11.5 weight percent $C_6$ paraffins, about 34.8 weight percent $C_7$ paraffins, about 42.5 weight percent $C_8$ paraffins, and about 10.4 weight percent $C_9$ paraffins was subjected to dehydrogenation employing a platinum-tin zinc aluminate catalyst having about 0.6 weight percent platinum and about 1.0 weight percent tin, based on the weight of the zinc aluminate. The catalyst was in the form of extrudate about 1/16 inch is diameter and about ¼ inch in length. The catalyst was placed in a reactor about 2 inches in diameter and about 8 inches in height. A catalyst bed of about 7 inches was employed.

The process was carried out by conducting dehydrogenation for thirty minutes, followed by a minute of purging, followed by 28 minutes of regeneration, followed by a minute of purging, followed by another dehydrogenation. The process was continued for 16 hours.

The steam to hydrocarbon molar ratio for the dehydrogenation steps was about 7.26. Hydrogen was included in the hydrocarbon feed. The molar ratio of hydrogen to hydrocarbon was about 0.48. The liquid hourly space velocity of hydrocarbon was about 4.09.

The flow rate of steam through the bed was maintained constant for all the steps.

After 16 hours the total conversion of $C_7$ paraffins was about 34.2 percent, of $C_8$ paraffins about 46 percent, and of $C_9$ paraffins about 72.9 percent.

Since the flow rate of steam was constantly the same it was possible to operate the steam preheater more efficiently. The purging of the catalyst bed before each regeneration of dehydrogenation helped to minimize the possibility that hydrocarbon and oxygen would react to form coke or otherwise inactivate the catalyst.

Various modifications can be made in view of this disclosure without departing from the spirit or scope of the invention.

What is claimed is:

1. A process for dehydrogenating a dehydrogenatable hydrocarbon feed using a bed of steam active dehydrogenation catalyst and repetitively regenerating said catalyst with steam and oxygen-containing gas wherein the flow rate of steam through the catalyst bed is maintained constant comprising, passing dehydrogenatable hydrocarbon feed through the catalyst bed under dehydrogenation conditions for a predetermined period of time, then stopping the flow of dehydrogenatable hydrocarbon to the catalyst bed, then after the steam has purged at least part of the dehydrogenatable hydrocarbon from the catalyst bed passing oxygen-containing gas through the catalyst bed under regeneration conditions for a period of time, then stopping the flow of oxygen-containing gas to the catalyst bed, then after the steam has purged at least part of the oxygen from the catalyst bed passing dehydrogenatable hydrocarbon through the catalyst bed under dehydrogenation conditions wherein more than one catalyst bed is employed and wherein dehydrogenation is conducted in one catalyst bed while regeneration is conducted in another and wherein the dehydrogenated hydrocarbon that is supplied to each catalyst bed is preheated by being passed in indirect heat exchange with the effluent from a catalyst bed that is being regenerated.

2. A process according to claim 1 wherein nitrogen is passed through the catalyst beds in conjunction with steam during the purging steps.

3. A process according to claim 2 wherein the dehydrogenatable hydrocarbon consists essentially of hydrocarbons boiling in the gasoline range.

4. A process according to claim 3 wherein the dehydrogenatable hydrocarbon consists essentially of hydrocarbons having 6 to 9 carbon atoms per molecule.

5. A process according to claim 4 wherein the inlet portion of the catalyst beds are maintained at a temperature in the range of about 950° F. to about 1,150° F. and the pressure is maintained in the range of 0 to 200 psig for both dehydrogenation and regeneration.

6. A process according to claim 5 wherein the dehydrogenation is conducted using a liquid hourly space velocity of dehydrogenatable hydrocarbon of about 1 to about 6 and steam to hydrocarbon mole ratio of about 1/1 to about 25/1 and the regeneration is carried out using steam containing about 0.5 to 2.5 mole percent of oxygen based on the moles of steam.

7. A process according to claim 5 wherein hydrogen is also passed through the catalyst bed during the dehydrogenation and wherein the mole ratio of hydrogen to dehydrogenatable hydrocarbon is about 0.3/1 to about 1.3/1.

8. A process according to claim 1 wherein the dehydrogenatable hydrocarbon consists essentially of hydrocarbons having 6 to 9 carbon atoms per molecule.

9. A process according to claim 8 wherein the inlet portion of the catalyst beds are maintained at a temperature in the range of about 950° F. to about 1,150° F. and the pressure is maintained in the range of 0 to 200 psig for both dehydrogenation and regeneration.

10. A process according to claim 9 wherein the dehydrogenation is conducted using a liquid hourly space velocity of dehydrogenatable hydrocarbon of about 1 to about 6 and steam to hydrocarbon mole ratio of about 1/1 to about 25/1 and the regeneration is carried out using steam containing about 0.5 to 2.5 mole percent of oxygen based on the moles of steam.

11. A process according to claim 10 wherein hydrogen is also passed through the catalyst bed during the dehydrogenation and wherein the mole ratio of hydrogen to dehydrogenatable hydrocarbon is about 0.3/1 to about 1.3/1.

12. A process according to claim 11 wherein said steam active dehydrogenation catalyst comprises (1) a support selected from the group consisting of alumina, silica, magnesia, zirconia, aluminasilicates, Group II aluminate spinels, and mixtures thereof and (2) a catalytic amount of at least one Group VIII metal selected from the group consisting of nickel, platinum, palladium, ruthenium, iridium, rodium, and osmium.

13. A process according to claim 12 wherein said support is zinc aluminate spinel, and said Group VIII metal is platinum, and said catalyst further includes tin in an amount in the range of about 0.01 to about 5 weight percent of said zinc aluminate spinel and wherein said platinum is present in an amount about 0.1 to about 5 weight percent of said zinc aluminate.

14. A process according to claim 7 wherein said steam active dehydrogenation catalyst comprises (1) a support selected from the group consisting of alumina, silica, magnesia, zirconia, aluminasilicates, Group II aluminate spinels, and mixtures thereof and (2) a catalytic amount of at least one Group VIII metal selected from the group consisting of nickel, platinum, palladium, ruthenium, iridium, rodium, and osmium.

15. A process according to claim 14 wherein said support is zinc aluminate spinel, and said Group VIII metal is platinum, and said catalyst further includes tin in an amount in the range of about 0.01 to about 5 weight percent of said zinc aluminate spinel and wherein said platinum is present in an amount about 0.1 to about 5 weight percent of said zinc aluminate.

* * * * *